(12) United States Patent
Batiste

(10) Patent No.: US 6,491,680 B1
(45) Date of Patent: Dec. 10, 2002

(54) CATHETER STRIPPING APPARATUS

(76) Inventor: Stanley Batiste, 9348 Buckhaven Dr., Las Vegas, NV (US) 89117

(*) Notice: Subject to any disclaimer, the term of this patent is extended or adjusted under 35 U.S.C. 154(b) by 92 days.

(21) Appl. No.: 09/686,479

(22) Filed: Oct. 10, 2000

(51) Int. Cl.[7] .............................................. A61M 25/00
(52) U.S. Cl. ..................................... 604/523; 606/113
(58) Field of Search ................................ 604/523, 264, 604/510, 93.01, 164.01, 164.13; 606/113, 106, 127, 110, 114, 119, 128, 222, 224, 139, 144, 1

(56) References Cited

U.S. PATENT DOCUMENTS

| | | | |
|---|---|---|---|
| 5,261,887 A | 11/1993 | Walker | 604/161 |
| 5,322,513 A | 6/1994 | Walker | 604/161 |
| 5,643,281 A | * 7/1997 | Suhocki et al. | 606/113 |
| 5,779,716 A | 7/1998 | Cano et al. | 606/114 |
| 5,800,444 A | 9/1998 | Ridinger et al. | 606/113 |

* cited by examiner

Primary Examiner—Anhtuan T. Nguyen
Assistant Examiner—Ann Y. Lam
(74) Attorney, Agent, or Firm—Henderson & Sturm LLP

(57) ABSTRACT

A catheter stripping apparatus (10) for removing a fibrin sheath (80) from the outlet end (101) of an indwelling access catheter (100) disposed in a patient's vascular system wherein the apparatus (10) includes: a stripping catheter unit (11) comprising an elongated hollow tubular housing member (20) having a rearwardly curved distal end (23) dimensioned to be received within the access catheter and further provided with an elongated soft pliably guide tip element (25); a wire noose unit (12) including an elongated strand of wire (30) dimensioned to be slidably received within the hollow tubular housing member (20) and having a distal end (31) provided with a wire noose element (32); and a retractor unit (13) for extending and retracting the wire noose element (32) relative to both the distal end of the hollow tubular housing member (20) and the outlet end (101) of the access catheter (100).

9 Claims, 4 Drawing Sheets

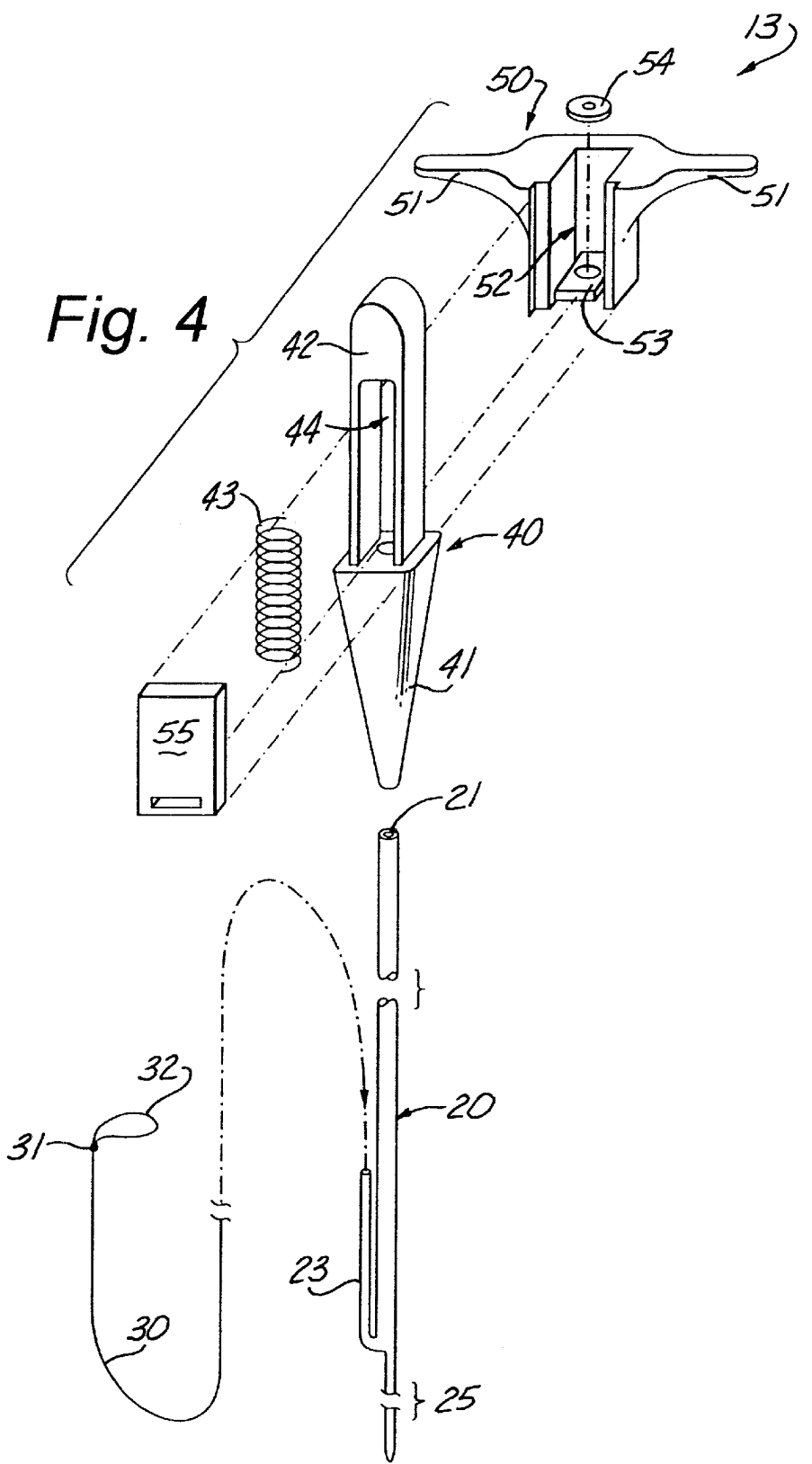

CATHETER STRIPPING APPARATUS

BACKGROUND OF THE INVENTION

1. Field of the Invention

The present invention relates to the field of surgical implements in general and in particular to a catheter stripping device for removing fibrin sheath.

2. Description of Related Art

As can be seen by reference to the following U.S. Pat. Nos. 5,643,281; 5,800,444; 5,261,887; 5,779,716 and 5,322,513; the prior art is replete with myriad and diverse catheter stripping arrangements for removing fibrin sheaths from the exterior of the catheter.

While all of the aforementioned prior art constructions are more than adequate for the basic purpose and function for which they have been specifically designed, they are uniformly deficient with respect to their failure to provide a simple, efficient, and practical catheter stripping apparatus that employs an extension guide element that will allow a surgeon to direct the stripping catheter safely into position while protecting the vascular system from injury during the medical procedure.

Unfortunately, while the prior art constructions recognize the problem of fibrin sheath build-up on indwelling access catheters, they have failed to address the trauma that is inflicted on the patient's vascular system through use of wire snare arrangements employed on their individual stripping catheters.

As a consequence of the foregoing situation, there has existed a longstanding need for a new and improved catheter stripping apparatus that not only quickly and easily strips a fibrin sheath from an indwelling access catheter, but also takes pains to protect the patient's vascular system during the stripping process; and, the provision of such an arrangement is the stated objective of the present invention.

BRIEF SUMMARY OF THE INVENTION

Briefly stated, the catheter stripping apparatus that forms the basis of the present invention comprises in general a stripping catheter housing unit, a wire noose unit at least partially contained within the stripping catheter housing unit and a retractor unit for controlling the position and deployment of the wire noose unit both with respect to the stripping catheter housing unit as well as the exterior surface of the indwelling access catheter.

As will be explained in greater detail further on in the specification, the stripping catheter housing unit including an elongated hollow tubular housing member having a rearwardly curved distal end that is dimensioned to be slidably received within an indwelling access catheter residing in a patient's vascular system wherein the rearwardly curved distal end of the housing member defines an elongated narrow slot that is adapted to captively engage the outlet end of the access catheter.

In addition, the distal end of the housing member is further provided with a downwardly depending soft pliable guide tip element that will facilitate the manipulation of the distal end of the housing member within the patient's vascular system in that the guide tip element will be the first portion of the housing member that encounters any resistance from contact with the walls of the patent's vascular system as the guide tip element exits from the outlet end of the access catheter.

Furthermore, the wire noose element includes an elongated strand of wire slidably disposed within the hollow tubular housing member and having a distal end provided with a wire noose element that surrounds the rearwardly curved distal end of the housing member and proximal end operatively associated with the retractor unit for extending and expanding as well as retracting and contracting the wire noose element and associated noose opening to accomplish the stripping of a fibrin sheath from the exterior surface of the access catheter.

BRIEF DESCRIPTION OF THE SEVERAL VIEWS OF THE DRAWINGS

These and other attributes of the invention will become more clear upon a thorough study of the following description of the best mode for carrying out the invention, particularly when reviewed in conjunction with the drawings, wherein:

FIG. 4 is an exploded perspective view of the catheter stripping apparatus; and, FIGS. 5A through 5E are sequential views of the plunger unit and the wire noose unit relative to both the access catheter and the stripping catheter housing unit during the fibrin sheath stripping procedure.

DETAILED DESCRIPTION OF THE INVENTION

Figure 1A:
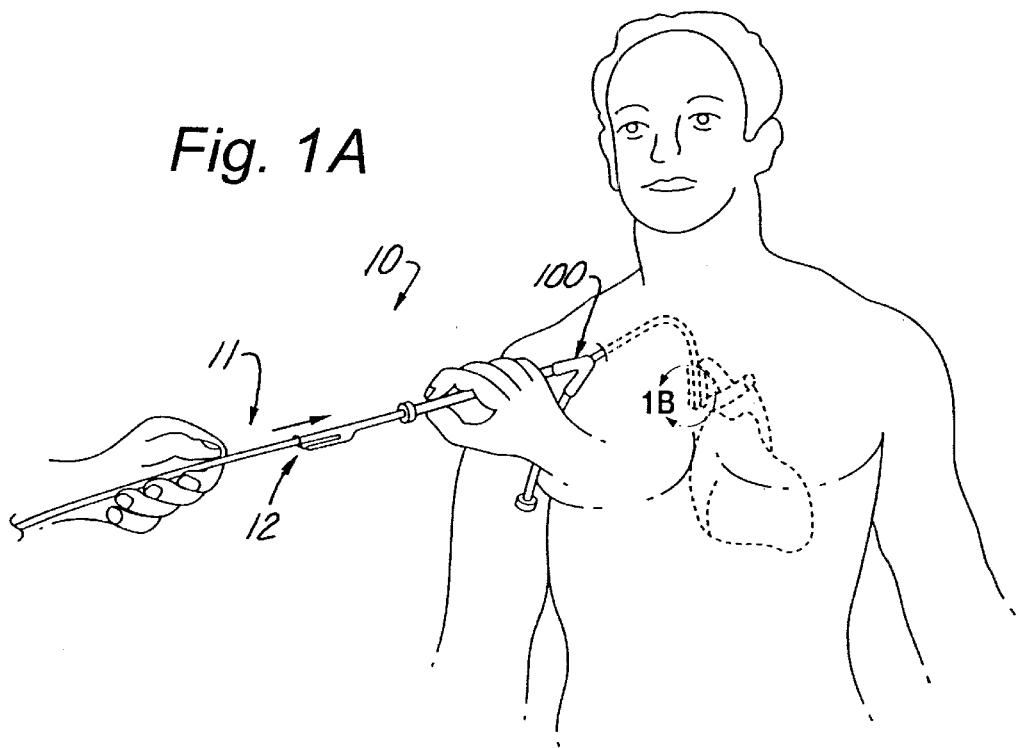
FIG. 1A is a perspective view of the catheter stripping apparatus of this invention being inserted into an access catheter disposed in an indwelling manner in the vascular system of a patent
Figure 1B:
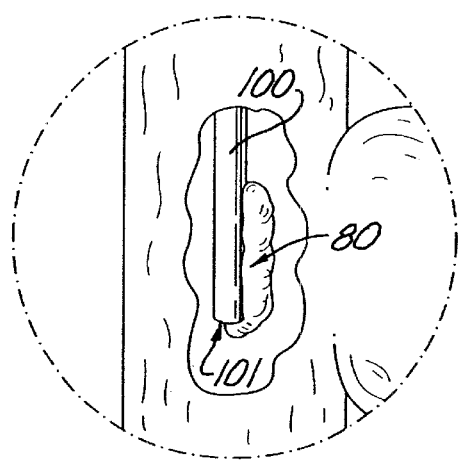
FIG. 1B is an enlarged detail view of a fibrin sheath that has formed on and occluded the distal end of an access catheter
Figure 2:
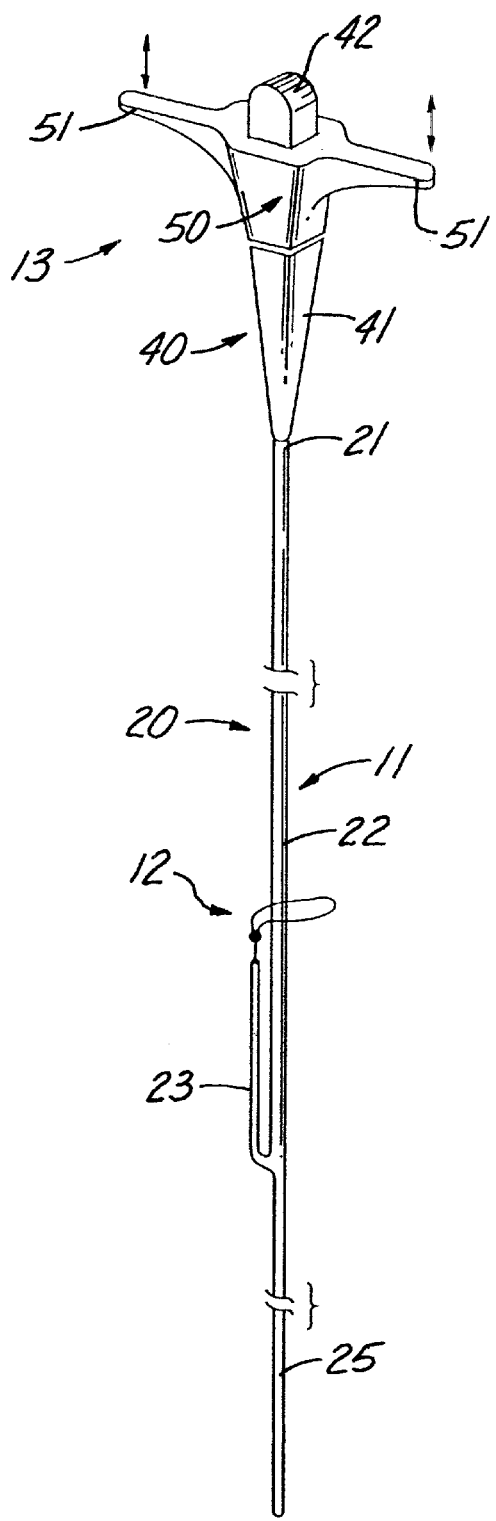
FIG. 2 is an isolated perspective view of the catheter stripping apparatus

As can be seen by reference to the drawings, and in particular to FIGS. 1 and 2, the catheter stripping apparatus that forms the basis of the present invention is designated generally by the reference number 10. The apparatus (10) comprises in general a stripping catheter housing unit (11) a wire noose unit (12) and a retractor unit (13). These units will now be described in seriatim fashion.

Figure 3:
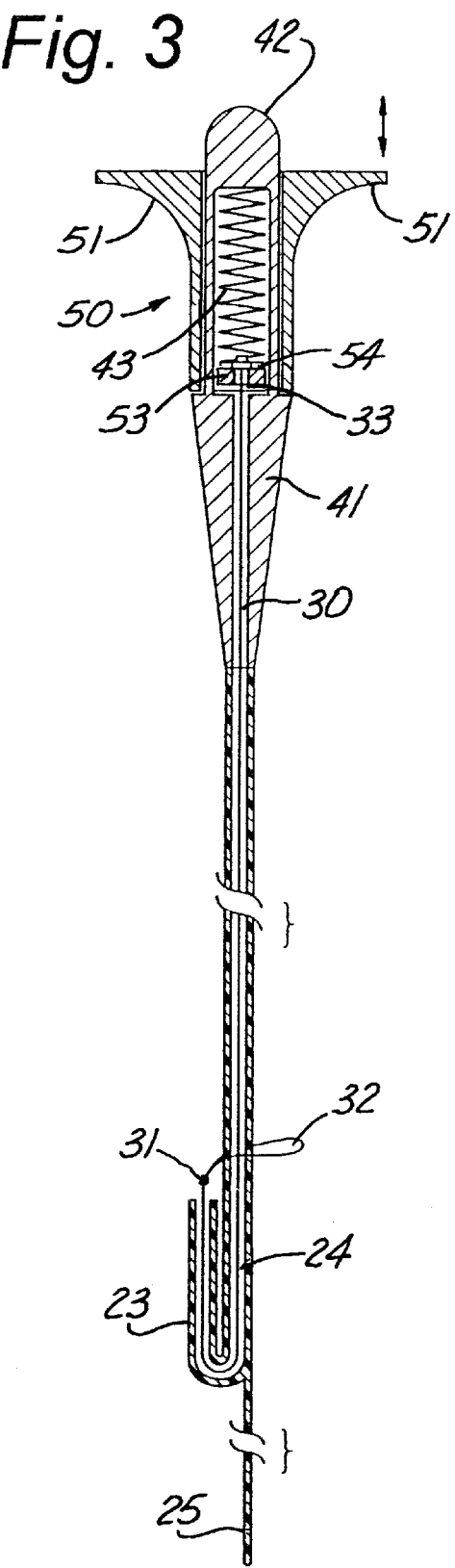
FIG. 3 is a cross-sectional view of the catheter stripping apparatus

As shown in FIGS. 2 through 4, the stripping catheter housing unit (11) comprises an elongated hollow tubular housing member (20) having a straight proximal end (21), an elongated straight intermediate portion (22) and a rearwardly curved distal end (23) wherein the interior of the tubular housing member (20) defines an elongated generally J-shaped passageway (24).

In addition, the distal end (23) of the housing member (20) is further provided with an elongated soft pliable guide tip element (25) which is generally aligned with the longitudinal axis of the stem portion of the J-shaped passageway (24) for reasons that will be explained in greater detail further on in the specification.

Furthermore, the rearwardly curved distal end (23) of the hollow tubular housing member (20) is provided with an extremely abrupt curvature so that the adjacent sections of the distal end (23) of the housing member (20) are disposed in close proximity to one another so as to allow the curved distal end (23) of the housing member (20) to pass through the interior of the access catheter (100).

Turning now to FIGS. 3 and 4, it can be seen that the wire noose unit (11) comprises an elongated strand of wire (30)

that is dimensioned to be received within and extend beyond the J-shaped passageway (24) in the housing member (20) wherein the distal end (31) of the wire strand (30) is provided with a noose element (32) and the proximal end (33) is operatively associated with the plunger unit (13).

Still referring to FIGS. 3 and 4, it can be seen that the retractor unit (13) comprises a housing member (40) having a hollow tapered lower portion (41) which is dimensioned to receive the proximal end (33) of the strand of wire (30), and to be operatively connected to the proximal end (21) of the tubular housing member (20); and, a reduce dimension generally inverted U-shaped upper portion (42) rigidly associated with the hollow tapered hower portion (41) dimensioned to receive a spring biasing element (43) whose pupose and function will be described presently.

In addition, the retractor unit (13) further comprises a retractor member (50) slidably disposed on the inverted U-shaped upper portion (42) of the housing member (40) and porvided with a pair of outwardly flared ginger grip elements (51) for withdrawing the retractor member (50) relative to the housing member (40).

As can best be seen by reference to FIG. 4, the retractor member (50) has an elnarged central recess (52) dimensioned to receive the upper portion (42) of the housing member (40); wherein the lower portion of the recess (52) has an apertured inwardly projecting foot element (53) dimensioned to be slidably received in the opening (44) in the upper poriton (42) of the housing member (40) for reasons that will be explained presently.

Returning once more to FIGS. 3 and 4, it can be seen that the retractor member (50) is further provided with a grommet (54) that is fixedly secured to the proximal end (33) of the elongated strand of wire (30) and rests upon the foot element (53) of the retractor member (50); wherein the influence of the spring biasing element (43) fully expands the size of the loop (32) at the distal end (34) of the strand of wire (30).

Figure 5A:
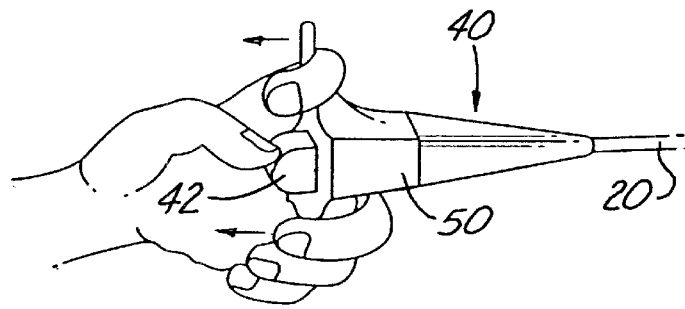
Figure 5C:
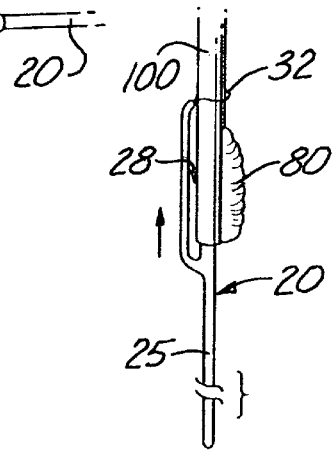
Figure 5B:
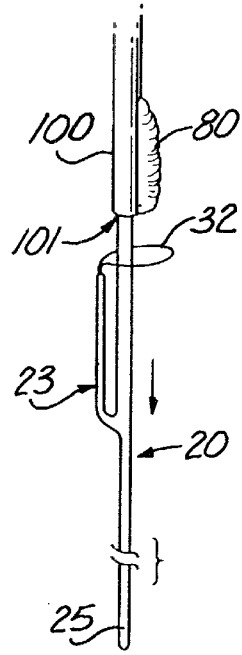

As can also appreciated by reference to FIGS. 5A through 5C when the retractor member (50) is with drawn relative to the retractor housing member (40) the wire noose element (32) will be fully withdrawn relative to the curved distal end (23) of the stripping catheter housing member (20); and, when the retractor member (50) is released, the wire noose element will fully expand under the influence of the spring biasing element (43).

The method employed by the catheter stripping apparatus (10) of this invention can best be appreciated by reference to FIGS. 1A and 5A through 5E wherein the tubular housing member (20) is first threaded through an entrance opening in an indwelling access catheter (100). At this stage the retractor unit (13) does not come into play until both the flexible guide probe (25) and the curved distal end (23) of the stripping catheter housing member (20) project beyond the outlet opening (101) of the access catheter (100).

Once the distal end (23) of the stripping catheter housing member (20) has cleared the outlet opening (101) of the access catheter (100), the retractor member (50) is still relaxed relative to the housing member (40) to fully extend and expand the wire noose element (32) as depicted in FIG. 5B.

The next step involves retracting the stripping catheter housing member (20) relative to the access catheter with the retractor member (50) still relaxed so that the wire noose element (32) will pass over the fibrin sheath (80) formed on the exterior of the access catheter (100).

At this juncture, the retractor member (50) is withdrawn relative to the housing (40) to retract the wire noose element (32) into engagement with the exterior walls of the access catheter (100) as depicted in FIG. 5C. It should also be noted by reference to FIG. 5C that the bottom of the narrow slot (28) formed by the rearwardly curved distal end (23) of the stripping catheter housing member (20) will limit the amount that the stripping catheter member (20) can be retracted relative to the access catheter (100) when the access catheter is received within the slot (28).

Figure 5D:
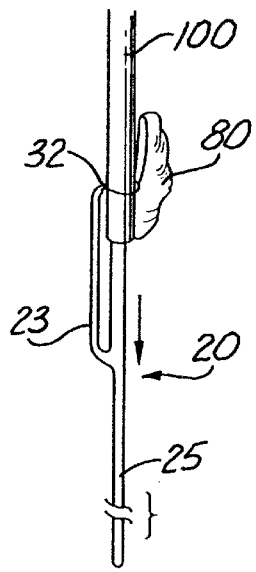
Figure 5E:
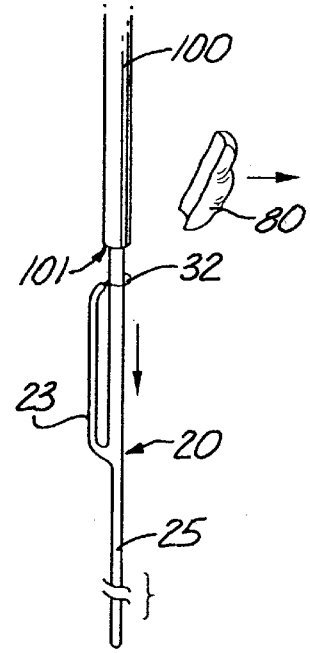

Once the wire noose element (32) engages the periphery of the access catheter (100), the stripping catheter body member (20) is extended once more relative to the access catheter (100) as shown in FIG. 5D so that the wire noose element (32) will strip the fibrin sheath (50) from the exterior of the access catheter. Then as the wire noose element passes over the outlet end (101 ) of the access catheter (100), the action of the compressed spring biasing element (46) will cause the wire noose element (32) to be retracted to the greatest extent possible prior to the surgeon releasing the retractor member (50) relative to the housing member (40) so that the stripping catheter unit (11) and the wire noose unit (12) can be readily withdrawn from the indwelling access catheter (100).

It should also be appreciated at this juncture that the presence of the soft pliable guide tip element (25) which extends downwardly from the curved distal end (23) of the stripping catheter housing member (20) allows the stripping catheter housing member (20) to be extended and retracted relative to the access catheter (100) with the minimum amount of abrasive contact being experienced by the patient's vascular system.

Although only an exemplary embodiment of the invention has been described in detail above, those skilled in the art will readily appreciate that many modifications are possible without materially departing from the novel teachings and advantages of this invention. Accordingly, all such modifications are intended to be included within the scope of this invention as defined in the following claims.

Having thereby described the subject matter of the present invention, it should be apparent that many substitutions, modifications, and variations of the invention are possible in light of the above teachings. It is therefore to be understood that the invention as taught and described herein is only to be limited to the extent of the breadth and scope of the appended claims.

I claim:

1. A catheter stripping apparatus for removing fibrin sheaths from the outlet end of an indwelling access catheter disposed in a patient's vascular system wherein the apparatus comprises:

a stripping catheter housing unit including an elongated hollow tubular housing member dimensioned to be slidably received in said access catheter and having a generally straight proximal end and intermediate portion and a rearwardly curved distal end which defines a narrow slot adapted to captively engage the outlet end of the access catheter a wire noose unit including an elongated strand of wire slidably disposed within the hollow tubular housing member and having a proximal end and a distal end provided with a noose element; and, first means associated with said wire noose unit for extending and retracting the noose element relative to the rearwardly curved distal end of the hollow tubular housing member and for expanding and contracting the opening in the wire noose element relative to both the distal end of the hollow tubular housing member and the outlet end of the access catheter, wherein, said first means comprises in part a spring biasing element operatively associated with the proximal end of the elongated strand of wire to retract the wire noose element relative to the rearwardly curved distal end of the hollow tubular housing member.

2. The apparatus as in claim 1 further comprising second means for guiding the rearwardly curved distal end of the hollow tubular housing member within the patient's vascular system.

3. The apparatus as in claim 2; wherein, the second means comprises an elongated soft pliable guide tip element that depends downwardly from the rearwardly curved distal end of the hollow tubular housing member.

4. The apparatus as in claim 3; wherein, the retractor member further includes:

a grommet that is fixedly secured to the proximal end of the elongated strand of wire; and an apertured foot element that projects inwardly from the enlarged central recess in the retractor member and which is dimensioned to receive the proximal end of the strand of wire and engage the grommet.

5. The apparatus as in claim 4, wherein, the retractor member is further provided with a plurality of outwardly flared finger grip elements.

6. The apparatus as in claim 1; wherein, said first means comprises:

a retractor unit including a retractor housing member having a hollow lower portion dimensioned to receive the proximal end of the strand of wire and an inverted U-shaped upper portion dimensioned to receive a spring biasing element that is operatively associated with the proximal end of the strand of wire; and, a retractor member having an enlarged central recess dimensioned to slidably receive the upper portion of the retractor housing member; wherein, the retractor member is associated with the spring biasing element and adapted to compress the spring biasing element to withdraw the proximal end of the strand of wire within the upper portion of the retractor housing member.

7. The apparatus as in claim 6; wherein, the retractor member further includes a grommet that is fixedly secured to the proximal end of the elongated strand of wire; and an apertured foot element that projects inwardly from the enlarged central recess in the retractor member and which is dimensioned to receive the proximal end of the strand of wire and engage the grommet.

8. The apparatus as claim 7; wherein, the retractor member is further provided with a plurality of outwardly flared finger grip elements.

9. A catheter stripping apparatus for removing fibrin sheaths from the outlet end of an indwelling access catheter disposed in a patient's vascular system wherein the apparatus comprises:

a stripping catheter housing unit including an elongated hollow tubular housing member dimensioned to be slidably received in said access catheter and having a generally straight proximal end and intermediate portion and a rearwardly curved distal end which defines a narrow slot adapted to captively engage the outlet end of the access catheter a wire noose unit including an elongated strand of wire slidably disposed within the hollow tubular housing member and having a proximal end and a distal end provided with a noose element; and, first means associated with said wire noose unit for extending and retracting the noose element relative to the rearwardly curved distal end of the hollow tubular housing member and for expanding and contracting the opening in the wire noose element relative to both the distal end of the hollow tubular housing member and the outlet end of the access catheter; wherein said first means comprises a retractor unit including a retractor housing member having a hollow lower portion dimensioned to receive the proximal end of the strand of wire and an inverted U-shaped upper portion dimensioned to receive a spring biasing element that is operatively associated with the proximal end of the strand of wire; and, a retractor member having an enlarged central recess dimensioned to slidably receive the upper portion of the retractor housing member; wherein the retractor member is associated with the spring biasing element and adapted to compress the spring biasing element to withdraw the proximal end of the strand of wire within the upper portion of the retractor housing member.

\* \* \* \* \*